United States Patent [19]

Dye

[11] Patent Number: 4,693,707
[45] Date of Patent: Sep. 15, 1987

[54] TAMPER DISCOURAGING DEVICE

[75] Inventor: John F. Dye, Elgin, Ill.

[73] Assignee: The Kendall Company, Boston, Mass.

[21] Appl. No.: 836,262

[22] Filed: Mar. 4, 1986

Related U.S. Application Data

[63] Continuation of Ser. No. 630,175, Jul. 12, 1984, abandoned.

[51] Int. Cl.⁴ ............................................. A61M 27/00
[52] U.S. Cl. ...................................... 604/111; 604/905
[58] Field of Search ................. 604/86, 111, 199, 240, 604/283, 905

[56]  References Cited

U.S. PATENT DOCUMENTS

| | | | |
|---|---|---|---|
| 3,332,418 | 7/1967 | Brody | 604/86 |
| 4,194,509 | 3/1980 | Pickering et al. | 604/111 |
| 4,436,125 | 3/1984 | Blenkush | 604/905 |
| 4,475,903 | 10/1984 | Steenhuisen et al. | 604/240 |

FOREIGN PATENT DOCUMENTS

| | | | |
|---|---|---|---|
| 50-23551 | 8/1975 | Japan | 604/111 |
| 2104044 | 3/1983 | United Kingdom | 604/111 |

Primary Examiner—C. Fred Rosenbaum
Assistant Examiner—Sherri E. Vinyard
Attorney, Agent, or Firm—Powell L. Sprunger

[57] ABSTRACT

A tamper discouraging device in a liquid drainage system comprising, an elastic catheter having an elongated shaft, a connector adjacent a proximal end of the catheter, and a drainage lumen extending through a major portion of the catheter and the connector. The device has a hollow drainage tube having a hollow adapter at an upstream end of the drainage tube, with the adapter being received in the catheter connector. The device has a circumferential band being heat shrunk against the catheter over the connector and adapter.

4 Claims, 3 Drawing Figures

TAMPER DISCOURAGING DEVICE

This is a continuation of application Ser. No. 630,175, filed on July 12, 1984 now abandoned.

BACKGROUND OF THE INVENTION

The present invention relates to liquid drainage systems.

Liquid drainage systems of the type which drain urine from a patient's bladder are known. Such systems generally comprise a catheter having a distal end received in the patient's bladder and a drainage lumen extending through the catheter, a hollow drainage tube, and a collection bag connected to a downstream end of the drainage tube, with an adapter at an upstream end of the drainage tube being received in a connector adjacent a proximal end of the catheter. In use, urine drains from the bladder through the catheter and drainage tube into the collection bag for collection therein.

Such drainage systems are sterile and are closed to the atmosphere to prevent bacteria from entering the system which otherwise might pass by retrograde movement into the bladder with possible deleterious results to the patient. In particular, it is undesirable to remove the adapter from the catheter connector since such a procedure could allow entry of bacteria into the system. Hence, it is desirable to discourage such disconnection, and, at the very least, if it is necessary to make the disconnection, such as for irrigation of the catheter, it is desirable to know when such a disconnection has taken place.

SUMMARY OF THE INVENTION

A principal feature of the present invention is the provision of an improved liquid drainage system.

In accordance with the present invention the liquid drainage system has a tamper discouraging device comprising, an elastic catheter having an elongated shaft, a connector adjacent a proximal end of the catheter, and a drainage lumen extending through a major portion of the shaft and the connector. The device has a hollow drainage tube having a hollow adapter at an upstream end of the drainage tube, with the adapter being received in the catheter connector. The device has a circumferential band being heat shrunk against the catheter over the connector and adapter.

A feature of the present invention is that the band discourages removal of the adapter from the catheter connector.

Yet another feature of the invention is that the band becomes dislodged in the event that the adapter is removed from the catheter connector.

Still another feature of the invention is that the dislodged band indicates when the adapter has been removed from the catheter connector.

Further features will become more fully apparent in the following description of the embodiments of this invention and from the appended claims.

DESCRIPTION OF THE PREFERRED EMBODIMENTS

Figure 1:
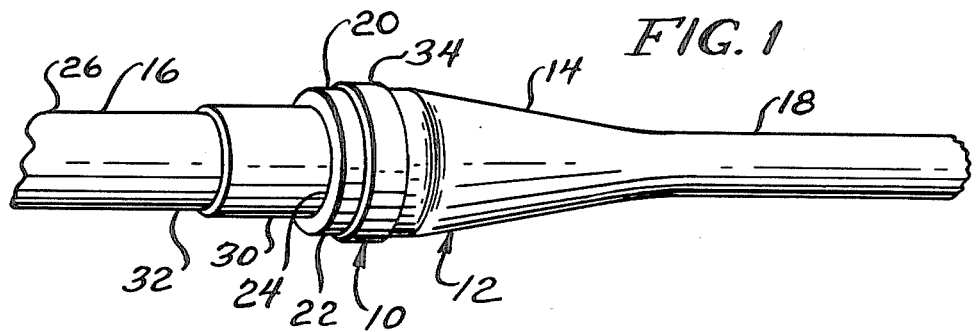
FIG. 1 is a fragmentary elevational view of a tamper discouraging device of the present invention.
Figure 2:
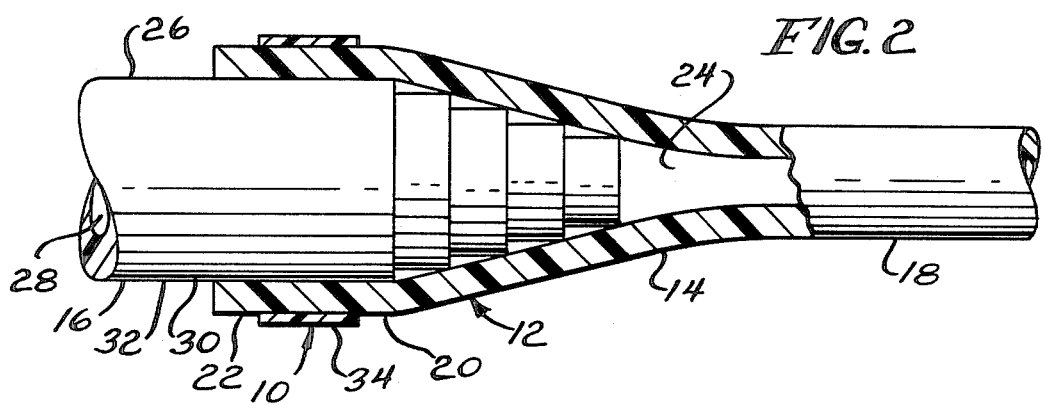
FIG. 2 is a fragmentary elevational view, taken partly in section, of the device of FIG. 1.

Referring now to FIGS. 1 and 2, there is shown a tamper discouraging device generally designated 10 in a liquid drainage system 12. The liquid drainage system 12 comprises an elastic catheter 14, and a hollow drainage tube 16.

The catheter 14 has an elongated elastic shaft 18, and an elastic connector 20 at a proximal end 22 of the catheter 14. The catheter 14 has a drainage lumen 24 extending through a substantial portion of the shaft 18 and through the connector 20.

The drainage tube 16 has an elongated conduit 26 having a lumen 28 extending therethrough. The drainage tube 16 has a hollow stepped adapter 30 at an upstream end 32 of the drainage tube 16. A collection bag (not shown) is connected to a downstream end (not shown) of the drainage tube 16. In use, the catheter shaft 18 is passed through the urethra of a patient until a distal end of the catheter 14 is located in the patient's bladder. Urine from the bladder drains through the catheter 14 and drainage tube 16 into the collection bag for retention therein.

As shown, the adapter 30 is received in the catheter connector 20 to permit drainage from the catheter 14 to the drainage tube 16. The system 12 is sterile prior to use, and is closed to the atmosphere to prevent the introduction of bacteria into the system 12 which might cause harmful results to the patient's bladder. Thus, it is undesirable to remove the adapter 30 from the catheter connector 20 since this procedure would expose the inside of the system 12 to the atmosphere with the possibility of entry of bacteria into the system 12.

In this regard, the system 12 has a circumferential tial band 34, such as polyethylene or polyvinyl chloride, which is heat shrunk against the catheter 14 over the catheter connector 20 and underlying adapter 30. In the event that the adapter 30 is removed from the catheter connector 20, the band 34 becomes dislodged, and it indicates that the adapter 30 has been removed from the connector 20 after reattachment of the adapter 30 to the connector 20. In this manner, it may be readily determined when the system 12 has been tampered with and exposed to the atmosphere.

Figure 3:
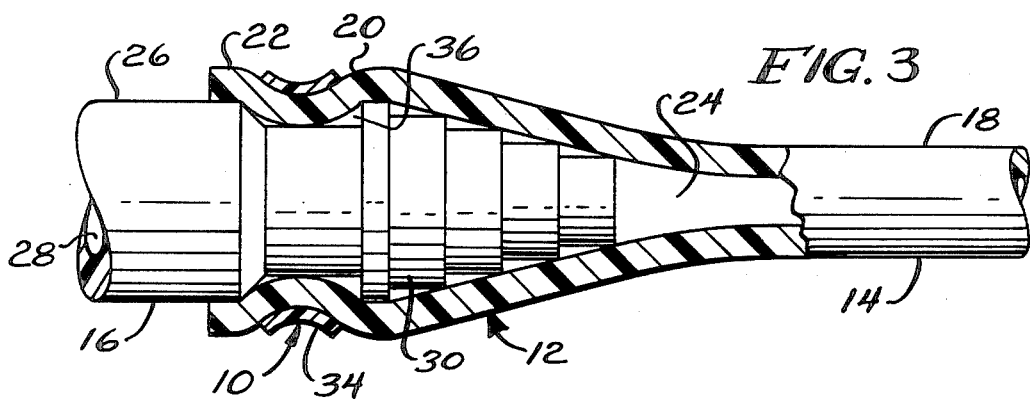
FIG. 3 is a fragmentary elevational view, taken partly in section, of another embodiment of the device of the present invention.

Another embodiment of the present invention is illustrated in FIG. 3, in which like reference numerals designate like parts. In this embodiment, the adapter 30 has a circumferential groove 36 underlying the band 34 which is preferably substantially inelastic. Thus, the elastic connector 20 is received in the adapter groove 36, and the band 34 is heat shrunk over the connector 20 in order to retain the catheter 14 in place on the adapter 30. In this embodiment, the band 34 prevents disengagement of the adapter 30 from the connector 20 unless the band 34 is removed, such as by cutting. Thus, in the event that the adapter 30 has been removed from the connector 20, the absence of the band 34 from the catheter 14 will indicate that the system 12 has been tampered with by removal of the adapter 30 from the connector 20.

The foregoing detailed description is given for clearness of understanding only, and no unnecessary limitations should be understood therefrom, as modifications will be obvious to those skilled in the art.

I claim:
1. A tamper discouraging device in a liquid drainage system, comprising:
   an elastic catheter having an elongated shaft, a connector adjacent a proximal end of the catheter, and a drainage lumen extending through a major portion of the shaft and the connector;
   a hollow drainage tube having a hollow adapter at an upstream end of the drainage tube, said adapter being received in the catheter connector; and
   a circumferential endless band being heat shrunk only against the catheter over said connector and adapter, said band being spaced from the adapter and an outer end of the connector, said band being free of adhesive.

2. The device of claim 1 wherein the band comprises polyethylene.

3. The device of claim 1 wherein the band comprises polyvinyl chloride.

4. The device of claim 1 wherein the band is substantially inelastic, and in which said adapter includes a circumferential groove beneath the band such that the connector is received in the groove beneath the band.

* * * * *